(12) United States Patent
Stamp

(10) Patent No.: US 7,635,356 B2
(45) Date of Patent: Dec. 22, 2009

(54) INJECTION DEVICE

(75) Inventor: Kevin Stamp, Sheffield (GB)

(73) Assignee: The Medical House, PLC (GB)

( * ) Notice: Subject to any disclaimer, the term of this patent is extended or adjusted under 35 U.S.C. 154(b) by 216 days.

(21) Appl. No.: 10/767,860

(22) Filed: Jan. 28, 2004

(65) Prior Publication Data

US 2005/0165360 A1 Jul. 28, 2005

(51) Int. Cl.
*A61M 5/00* (2006.01)
(52) U.S. Cl. .................. 604/187; 604/136; 604/134; 604/117
(58) Field of Classification Search .................. 604/187, 604/503, 155, 110, 116, 186, 131–136, 157, 604/117
See application file for complete search history.

(56) References Cited

U.S. PATENT DOCUMENTS

| | | | |
|---|---|---|---|
| 3,811,442 A | 5/1974 | Maroth | |
| 4,617,016 A * | 10/1986 | Blomberg | 604/155 |
| 4,958,622 A | 9/1990 | Selenke | |
| 4,976,724 A | 12/1990 | Nieto et al. | |
| 5,024,656 A | 6/1991 | Gasaway et al. | |
| 5,042,977 A | 8/1991 | Bechtold et al. | |
| 5,078,698 A | 1/1992 | Stiehl et al. | |
| 5,211,625 A | 5/1993 | Sakurai et al. | |
| 5,300,030 A * | 4/1994 | Crossman et al. | 604/136 |
| 5,478,316 A * | 12/1995 | Bitdinger et al. | 604/135 |
| 5,634,906 A | 6/1997 | Haber et al. | |
| 5,658,261 A | 8/1997 | Neer et al. | |
| 5,681,291 A | 10/1997 | Galli | |
| 5,779,675 A | 7/1998 | Reilly et al. | |
| 6,270,479 B1 * | 8/2001 | Bergens et al. | 604/156 |
| 6,280,421 B1 | 8/2001 | Kirchhofer et al. | |
| 6,544,234 B1 * | 4/2003 | Gabriel | 604/207 |

(Continued)

FOREIGN PATENT DOCUMENTS

EP 0453212 4/1991

(Continued)

OTHER PUBLICATIONS

PCT Written Opinion of the International Searching Authority corresponding to International Application No. PCT/GB2005/000223, Jun. 22, 2005, 7 pages.

(Continued)

*Primary Examiner*—Kevin C Sirmons
*Assistant Examiner*—Phillip Gray
(74) *Attorney, Agent, or Firm*—Sheridan Ross P.C.

(57) ABSTRACT

An injection device comprising an outer housing inside which is located a medicament-holding barrel with a needle at one end thereof, at least part of the needle being moveable in and out of the outer housing, a plunger moveable within the barrel, an inner housing intermediate the outer housing and the barrel and plunger and an energy source in communication with said inner housing. The inner housing is moveable by the energy source between
    a first position in which the plunger and barrel are movable axially so as to move at least part of said needle out of the outer housing;
    a second position in which the plunger is movable axially into said barrel so as to expel medicament through the needle; and
    a third position in which the plunger and barrel are able to retract in order to retract the needle into the outer housing.

16 Claims, 12 Drawing Sheets

U.S. PATENT DOCUMENTS

| | | | |
|---|---|---|---|
| 6,620,137 | B2 | 9/2003 | Kirchhofer et al. |
| 6,702,608 | B2 | 3/2004 | Brennan, Jr. |
| 6,752,781 | B2 | 6/2004 | Landau et al. |
| 7,156,823 | B2 | 1/2007 | Landau et al. |
| 2001/0004681 | A1 | 6/2001 | Landau |
| 2001/0053886 | A1 | 12/2001 | Caizza ........................ 604/110 |
| 2003/1000052 | * | 1/2003 | Anderson et al. ...... 128/203.23 |
| 2003/0045858 | A1 | 3/2003 | Struys et al. ................. 604/503 |
| 2005/0165349 | A1 | 7/2005 | Stamp |
| 2007/0173770 | A1 | 7/2007 | Stamp |

FOREIGN PATENT DOCUMENTS

| | | |
|---|---|---|
| EP | 0518416 | 12/1992 |
| EP | 1323477 | 7/2003 |
| EP | 1323447 | 8/2003 |
| GB | 886444 | 1/1962 |
| GB | 2396298 A | 6/2004 |
| GB | 2410188 | 7/2005 |
| WO | WO 99/22792 | 5/1999 |
| WO | 0009186 | 2/2000 |
| WO | 019/3926 A2 | 12/2001 |
| WO | 02/070051 A1 | 9/2002 |
| WO | 03/099358 A3 | 12/2003 |
| WO | 2005/070481 A1 | 8/2005 |
| WO | 2005/097252 | 10/2005 |
| WO | WO 2005/115507 | 12/2005 |
| WO | 03097133 | 7/2006 |
| WO | WO 2006/106291 | 10/2006 |
| WO | WO 2006/106295 | 10/2006 |

OTHER PUBLICATIONS

PCT Preliminary Report on Patentability corresponding to International Application No. PCT/GB2005/000223, Jan. 23, 2006, 13 pages.
UK Search Report for Application GB0602411.1, dated Apr. 6, 2006.
Corrected Search Report under Section 17, GB0620163.6, Nov. 24, 2006, Mr. Jeremy Cowen, 1 page.
Office Action for U.S. Appl. No. 10/767,859, dated Feb. 24, 2006, 9 pages.
Office Action for U.S. Appl. No. 10/767,859, dated Sep. 12, 2006, 13 pages.
Office Action for U.S. Appl. No. 10/767,859, dated Jun. 5, 2007, 8 pages.
Official Action for U.S. Appl. No. 10/767,859, mailed Dec. 28, 2007, 8 pages.
U.S. Appl. No. 10/597,379, filed Jul. 21, 2006, Stamp.
U.S. Appl. No. 12/161,776, filed Jul. 22, 2008, Stamp.
International Search Report for International (PCT) Patent Application No. PCT/GB2007/000141, mailed May 5, 2007, pp. 1-2.
Written Opinion for International (PCT) Patent Application No. PCT/GB2007/000141, mailed May 5, 2007, pp. 1-7.
Authorized Officer Mulhausen, International Preliminary Report on Patentability for International (PCT) Patent Application No. PCT/GB2007/000141, dated Jul. 29, 2008.
UK Search Report for Application No. GB0620163.6, dated Nov. 24, 2006, 1 page.
Official Action for U.S. Patent Application No. , mailed Jul. 31, 2008, 12 pages.
Restriction Requirement for U.S. Appl. No. 11/387,645, mailed May 28, 2009, 7 pages.
Official Action for U.S. Appl. No. 10/597,379, mailed Feb. 23, 2009, 9 pages.

* cited by examiner

INJECTION DEVICE

This invention relates to the field of injection devices for the administration of liquid medication, for example, insulin or growth hormone.

One type of injection device is known as a mini-needle or micro-needle device. These devices comprise a pressurised ("forced") injection system and have a needle which is shorter than that of conventional needle systems. The needle is normally hidden which is advantageous both for avoiding needle stick injuries and for minimising trauma to needle-phobic patients. The needle is hidden both before and after the injection is delivered, appearing only for the duration of the injection. Mini needle devices can typically deliver a larger volume of medication than needle-free devices and can deliver faster than conventional needle systems.

One such known device is described in WO00/09186 (Medi-Ject Corporation) for "Needle assisted jet injector" and this document gives a useful summary of prior art devices.

The device of WO 00/09186 includes a needle which is, in one embodiment, retractably located within an injector nozzle assembly. Upon activation of a force generating source, a portion of the needle extends past the nozzle assembly and penetrates the outer layer of skin to deliver medicament via jet injection to a deeper region. After activation, the needle retracts back into the nozzle assembly. The retractable needle is housed within the nozzle and is pushed forward so that it emerges in order to deliver an injection by the liquid medicament itself, when the medicament is itself pushed forward by the plunger.

According to a first aspect of the present invention there is provided an injection device comprising an outer housing inside which is located
- a barrel for holding a dose of a medicament;
- a needle at one end the barrel and fixed with respect thereto, the needle and barrel being such that at least part of the needle is axially moveable in and out of said outer housing but is biased to be normally wholly inside said housing;
- a plunger, axially moveable within the barrel;
- an inner housing intermediate the outer housing and the barrel and plunger; and
- an energy source in communication with said inner housing,
- wherein the inner housing is moveable by the energy source between three positions, namely a first position in which the inner housing is in communication with both the plunger and the barrel such that, in use, the plunger and barrel are movable axially so as to move at least part of said needle out of the outer housing;
- a second position in which the inner housing is in communication with the plunger but not the barrel such that, in use, said plunger is movable axially into said barrel so as to expel medicament through the needle; and
- a third position in which the inner housing is in communication with neither the plunger nor the barrel such that, in use, the plunger and barrel are able to retract in order to retract the needle into the outer housing.

The injection device according to the present invention provides a simple and cost-effective means of delivering medicament through a retractable mini needle. The device is able to deliver medicament to a depth beyond the length of the needle because of the propulsive force provided by the energy source.

The device requires that the needle (and hence also the barrel to which it is fixed) is moved axially so that the needle can appear beyond the end of the nozzle for the duration of the injection, after which the needle retracts automatically, out of sight of the user. The device also requires that the plunger is moved axially (into the barrel) so that medicament is ejected. The overall complexity of the injection device is significantly reduced by both of these requirements being effected by one component, namely the inner housing.

Preferably, said inner housing includes one or more flexible tags, biased radially inwardly by communication with said outer housing.

Preferably, one or more of said tags are situated at the rear end of the inner housing and are biased radially inwardly into communication with the plunger. Each rear tag may be moveable out of communication with the plunger when aligned with a corresponding recess in the outer housing. Preferably, each rear tag is substantially T-shaped. One leg of the T-shape enables the rear tag to hook over the plunger and, effectively, pull the plunger forward (in the first and second positions mentioned above). The other leg of the T-shape enables the rear tag to spring radially outwardly to catch in a recess in the housing (in the third position mentioned above).

Preferably, one or more of said tags are situated at the forward end of the inner housing and are biased radially inwardly into communication with the barrel. Each forward tag may be moveable out of communication with the barrel when aligned with a corresponding recess in the outer housing. Preferably, each rear tag is substantially L-shaped.

In a preferred embodiment, said energy source is a compressed gas.

Preferably, the injection device further includes means for allowing the inner housing to move axially only forward with respect to the outer housing. Ideally, said means is an arrangement of serrations intermediate the housings.

Preferably, said needle is biased to be normally wholly inside said housing by means of a spring intermediate the barrel and the outer housing.

In one embodiment, said needle, barrel and plunger are removable from said device.

Preferably, the injection device further includes a removable needle cover which protects the needle during storage and before use. Advantageously, said needle cover includes means for pulling a protective rubber sheath or the like from said needle when said needle cover is removed from the device.

According to a second aspect of the invention, there is provided a method of delivering an injection using an injection device as described in any of the preceding paragraphs.

Preferred embodiments of the present invention will now be more particularly described, by way of example only, with reference to the accompanying drawings wherein:

FIG. 1 is a perspective view, partly in section, showing the injection device, in the condition in which it is supplied to a user, apart from the needle cover;

FIG. 2, drawn to a larger scale, shows detail of part of the device shown in FIG. 1;

FIG. 3 is a perspective view, partly in section, showing the injection device, during an injection;

FIG. 4, drawn to a larger scale, shows detail of part of the device shown in FIG. 3;

FIG. 5 is a perspective view, partly in section, showing the injection device, with the plunger fully depressed into the barrel;

FIG. 6, drawn to a larger scale, shows detail of part of the device shown in FIG. 5;

FIG. 7 is a perspective view, partly in section, showing the injection device, after use and safe to dispose of;

FIG. 8, drawn to a larger scale, shows detail of part of the device shown in FIG. 7;

Throughout the following description, reference to a "forward" direction means the direction which is towards the patient when the injection device is in use. The "forward" end of the injection device is the end nearest the patient's skin when the device is in use. Similarly, reference to a "rearward" direction means the direction which is away from the patient and the "rearward" end of the device is the end furthest from the patient's skin when the injection device is in use.

Figure 1:
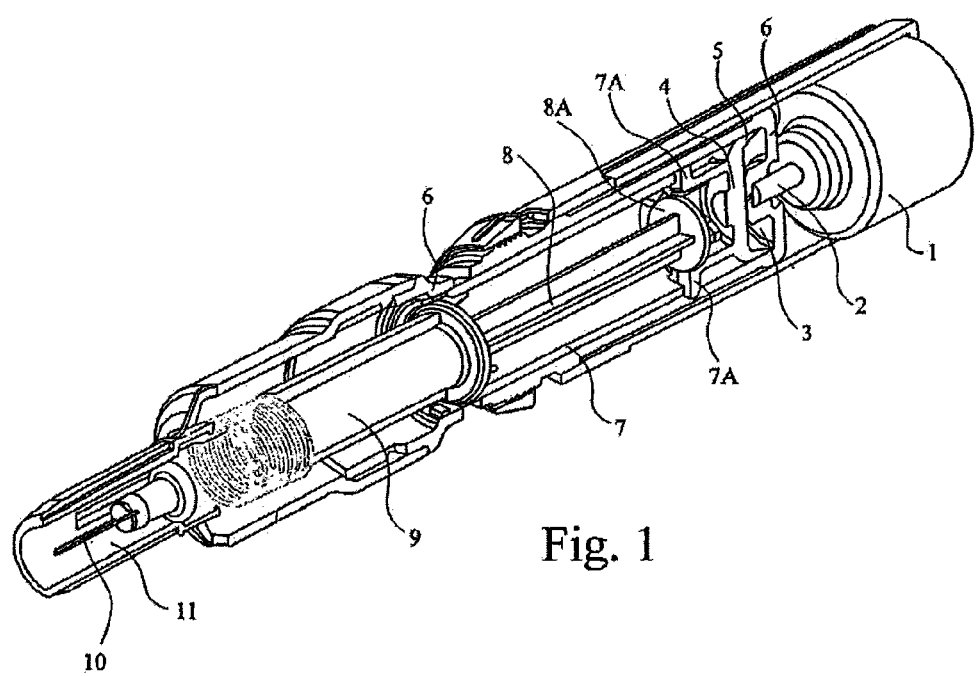

FIG. 1 is a perspective view, partly in section, showing the injection device, in the condition in which it is supplied to a user, apart from the needle cover (which is described below after the main operation of the device).

The principal components of the device will now be described with reference to FIGS. 1 and 2. An energy source 1 is provided at the rear of the device which, in this embodiment, is a gas cylinder similar to the type used in a conventional aerosol can or the like i.e. having a valve through which gas can be released at will and in a controlled manner. In an alternative embodiment of the invention, it is envisaged that a spring could be used as the energy source in place of a gas cylinder.

The valve 2 of the gas cylinder opens into a chamber 3, which in FIG. 1 is of relatively small volume. The front wall of the chamber 3 is defined by a ram 4 which has an annular seal 5 at the rear thereof in order to make the chamber 3 gas-tight. The rear wall of the chamber 3 is defined by the back face of a generally cylindrical chamber housing 6.

Figure 12:
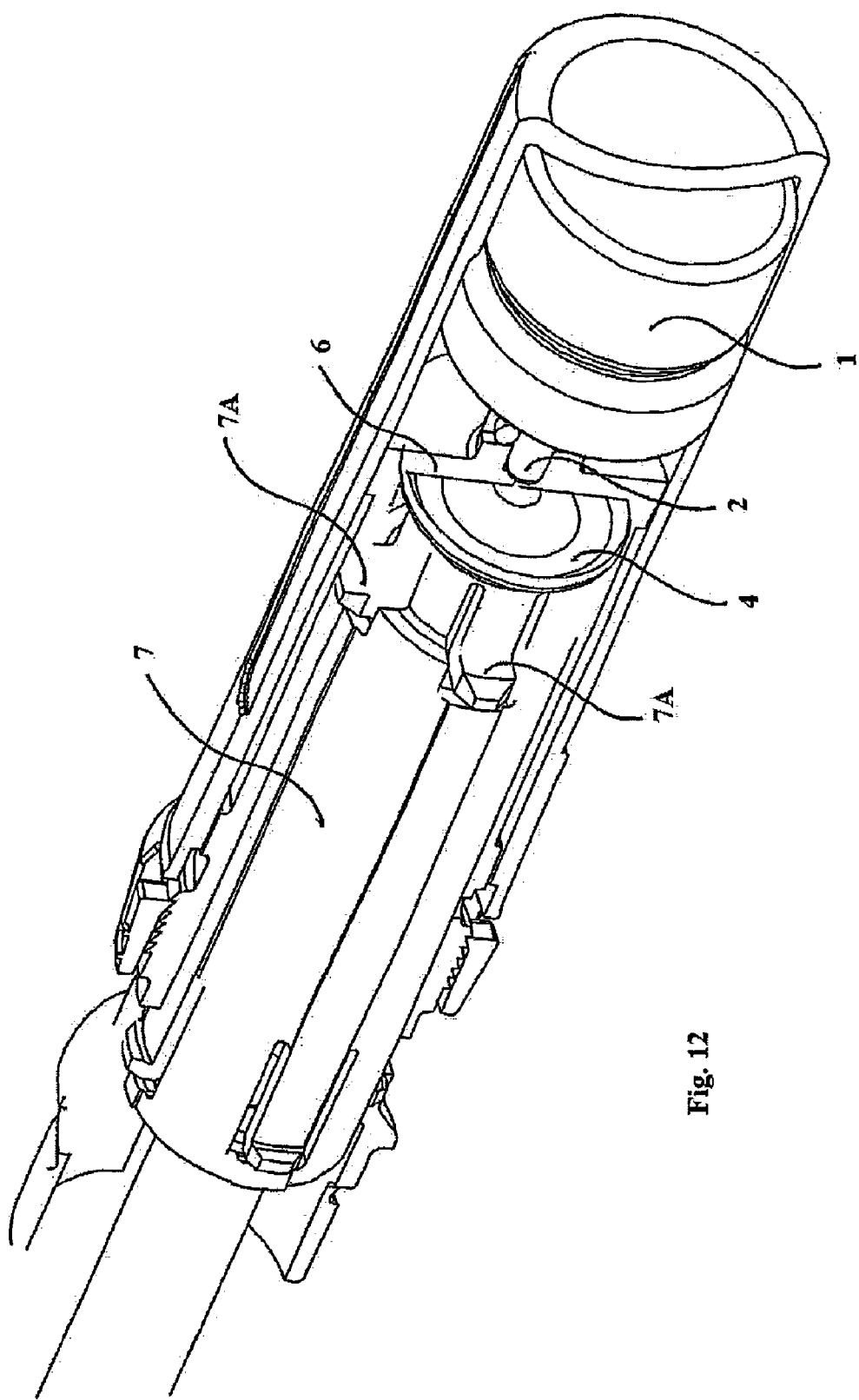
FIG. 12 is a schematic view showing the relationship between tags 7A and ram 4, in one embodiment of the invention.

The forward part of the ram 4 abuts or alternatively is integrally-formed with an inner housing 7 which closely surrounds a plunger 8 (and can therefore be referred to as the "plunger housing"). The rear of the plunger housing includes four orthogonally placed tags 7A, which each have a "hammer head" or T-shape and whose tendency to spring radially outwardly is restricted by the diameter of the chamber housing 6. If the ram 4 is integrally formed with the plunger housing 7 as illustrated in FIG. 12, the tags 7A are positioned at the end of flexible legs cut into the housing, so that the tags 7A can move radially, with respect to the ram 4 and remainder of housing 7.

Figure 2:
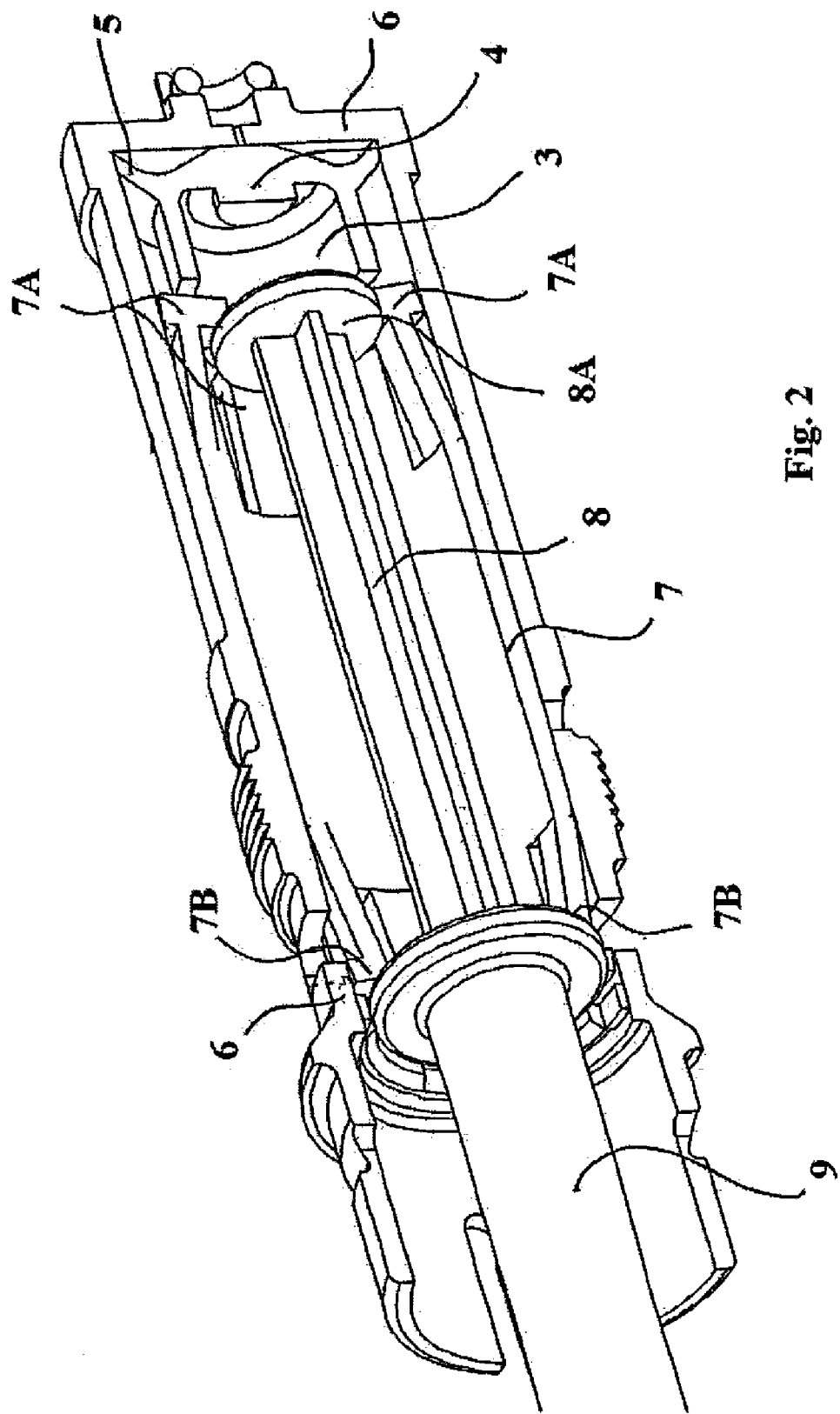

The hammer head of each tag 7A hooks over the enlarged head 8A of the plunger 8, so that the tags 7A are in contact with the plunger head 8A, as shown best in FIG. 2.

The plunger 8 is the plunger of a syringe arrangement comprising a barrel 9 in which a predefined dose of liquid medicament is supplied and a relatively short needle 10 through which the medicament can be delivered to the patient. A nozzle 11 at the front end of the injection device normally conceals the needle 10 from the user's view. A spring 12, positioned between the outer housing and the barrel 9 biases the needle to be normally wholly within the nozzle 11.

At the front end of the plunger housing 7, there are further orthogonally placed tags 7B, which each have a generally L shape and whose tendency to spring radially outwardly is restricted by the diameter of the chamber housing 6. The tags 7B each abut the flange at the rear of barrel 9.

There are four main stages in the operation of the device. Stage 1 is the condition shown in FIGS. 1 and 2, i.e. the device as supplied to a user, and as described above. The medicament is already present in the barrel 9 and the needle 10 is concealed from view within the nozzle 11. The plunger 8 is fully withdrawn from the barrel 9 (because of the liquid medicament contained within the barrel) and the head of the plunger 8A abuts the tags 7A. The rear of the remainder of housing 7 abuts the ram 4. The chamber 3 is of minimal volume.

Figure 3:
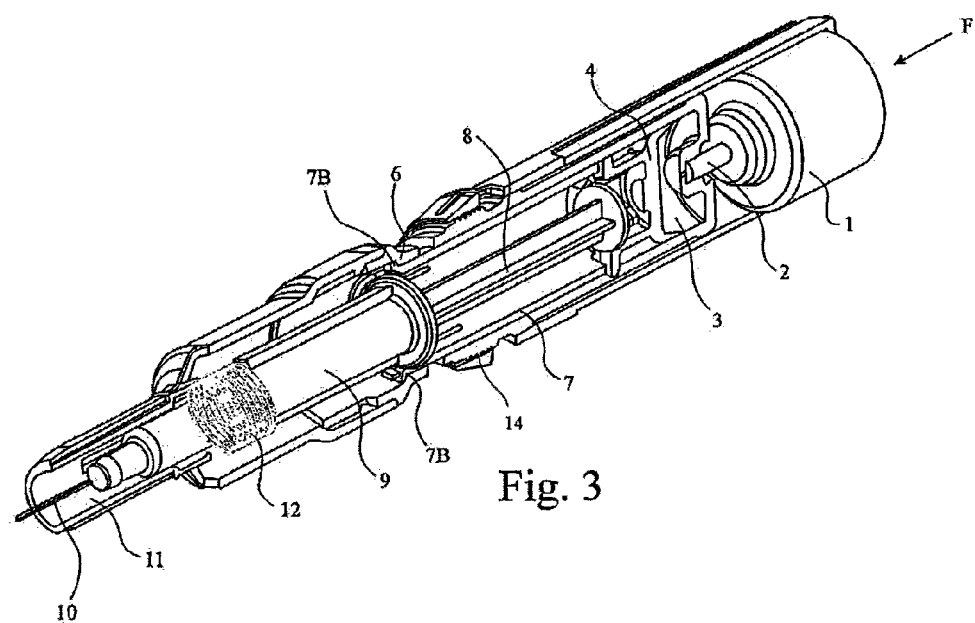
Figure 4:
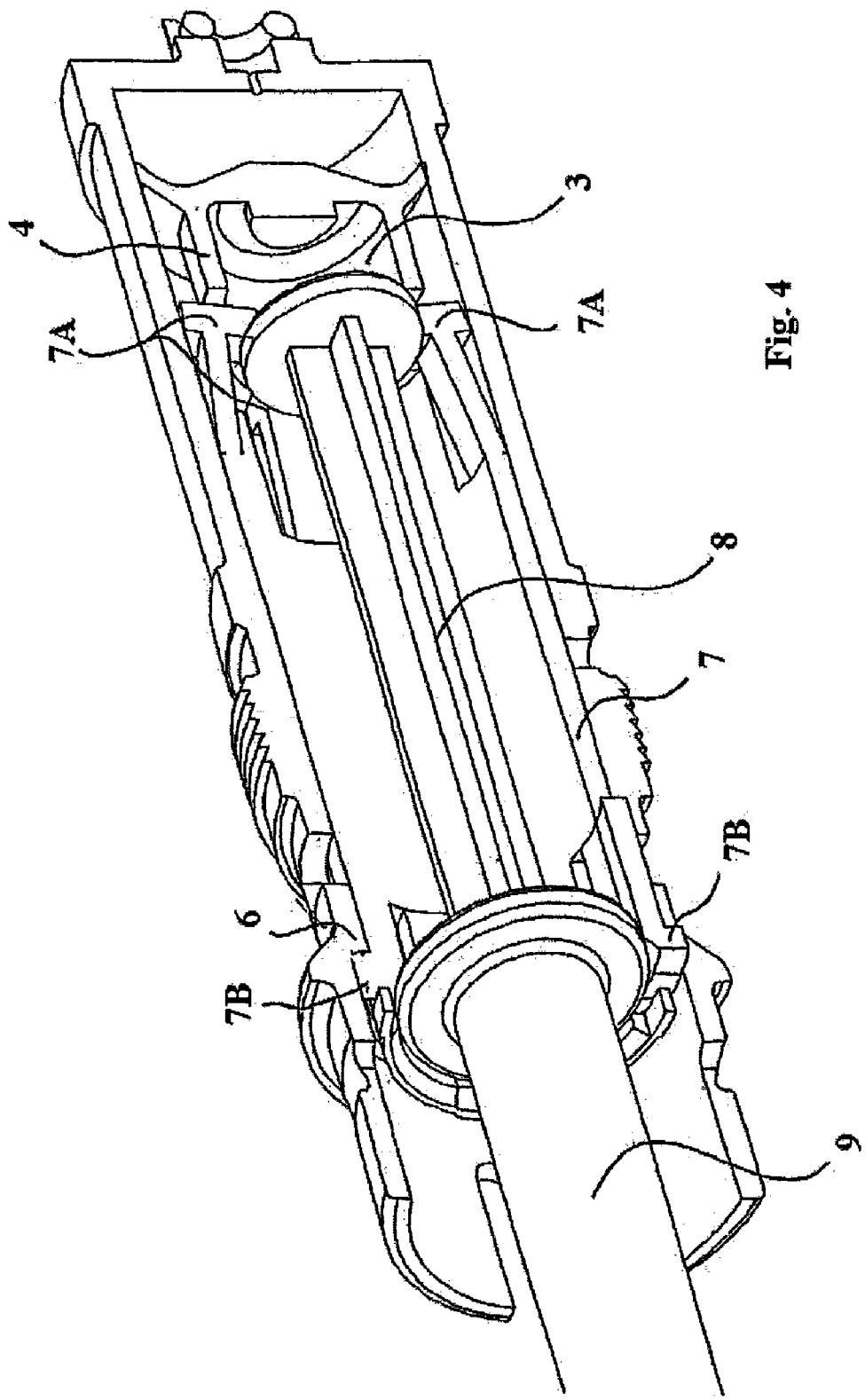

Stage 2 of operation is the injection stage illustrated in FIGS. 3 and 4. With the injection device held against the patient's skin at the injection site, downward force is applied to the device in the direction indicated by the arrow F in FIG. 2. This force causes the valve of the gas cylinder 1 to open, releasing gas into the chamber 3. As the chamber 3 fills with gas, the ram 4 is urged forward, consequently urging tags 7A against the plunger 8. As the tags 7A, and hence the plunger housing 7, are urged forward, the cooperation of the tags 7B against the barrel 9 means that the barrel is also urged forward, against the bias of a spring 12 (shown in FIG. 3). As the barrel 9 moves forward, so does the needle 10 which is attached thereto and so the needle protrudes out of the nozzle 11 sufficiently to enable an injection to be delivered. Therefore, initially, the ram 4 causes the plunger housing 7, the plunger 8, the barrel 9 and the needle 10 to move forwards.

Shortly after the plunger housing 7 starts to move forward, the tags 7B reach a lip in the chamber housing 6. The tags 7B spring radially outwardly over this lip, as shown in FIGS. 3 and 4. Once the tags 7B have sprung outwardly in this way, they are no longer in abutment with the barrel 9. This means that the barrel 9 (and hence needle 10) is no longer urged forwards because the forwardly-moving plunger housing 7, including tags 7B, are free to continue moving forward without contacting the barrel 9.

Therefore, once the device has reached the condition illustrated in FIGS. 3 and 4, continued forward movement of the ram 4 and plunger housing 7 causes the plunger 8 to be urged forward into the barrel 9. This expels the liquid medicament from the barrel 9, through the needle 10 to deliver an injection. It is the cooperation of the tags 7A with the enlarged head 8A of the plunger which transmits the forward force from the ram 4/housing 7 to the plunger 8.

Figure 5:
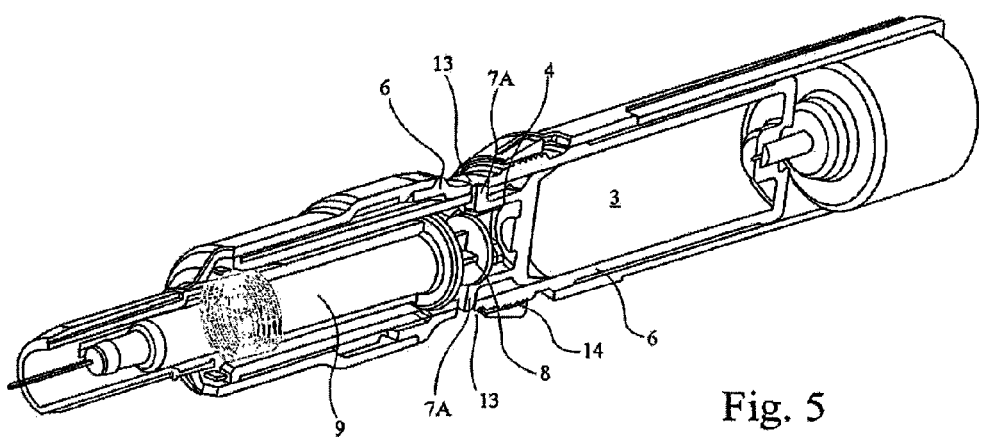
Figure 6:
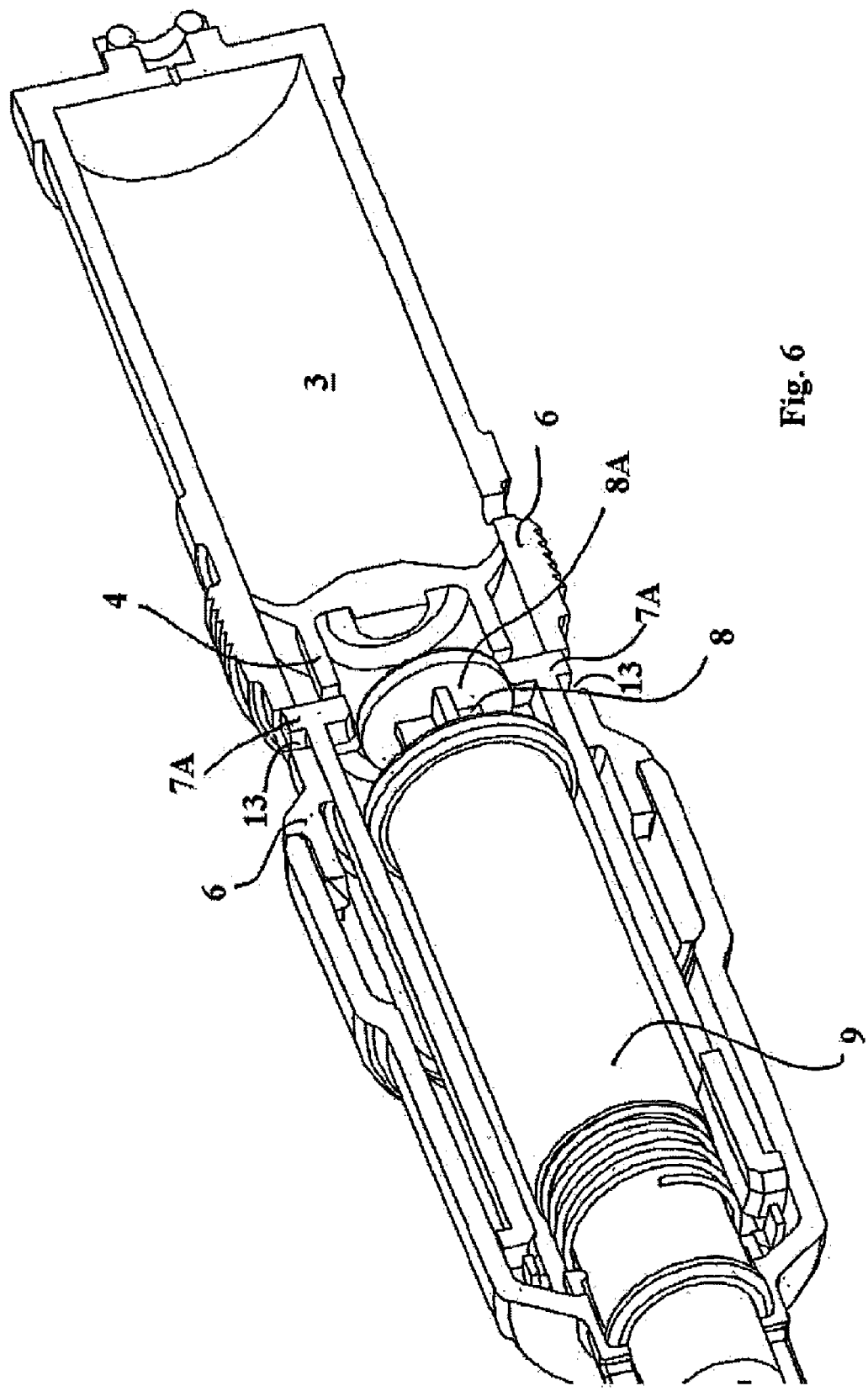

The third stage in the operation of the device is illustrated in FIGS. 5 and 6. When the plunger 8 is fully depressed into the barrel 9, the full dose of medicament has been delivered into the patient. At this point, the tags 7A reach recesses 13 cut into the plunger housing 6 whereupon they are able to spring radially outwardly into those recesses (as illustrated in FIGS. 5 and 6). This outward movement of the tags 7A means that the "hammer head" shape is no longer in contact with the enlarged head 8A of the plunger 8 and therefore the plunger 8 is no longer driven forward by the ram 4 and tags 7A. The plunger housing 7 may continue further forward until an end stop is reached.

Figure 7:
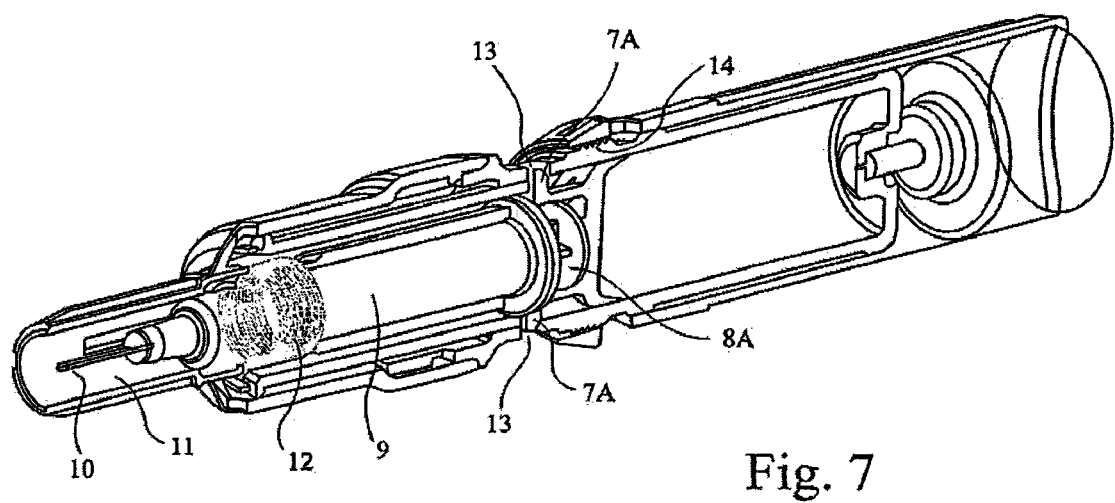
Figure 8:
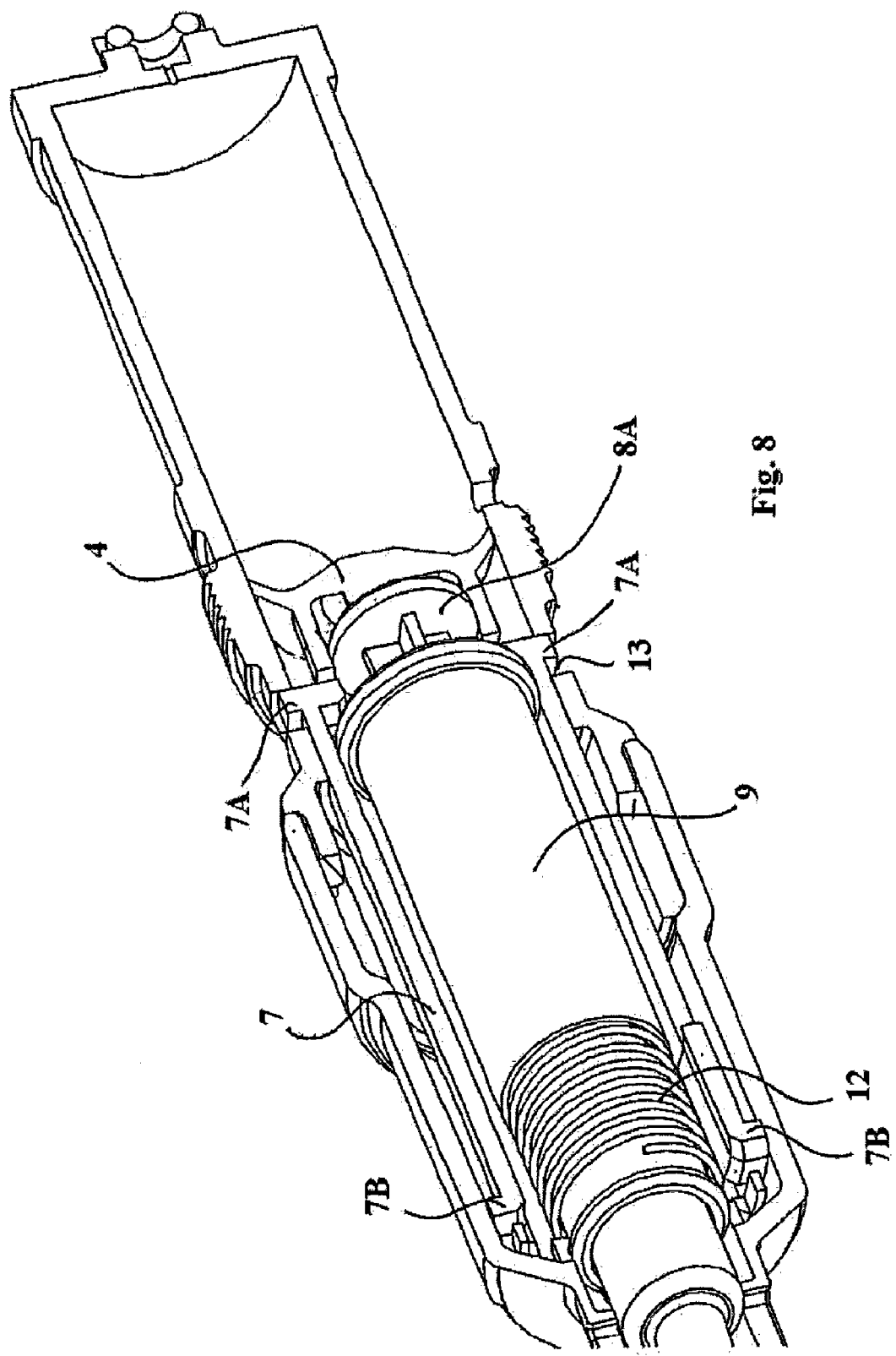

The final stage in the operation of the device is illustrated in FIGS. 7 and 8. With the tags 7A located within recesses 13, neither the plunger 8 or the barrel 9 is impeded by any part of the plunger housing 7. Therefore the spring 12, which had been compressed by the forward motion of the barrel 9, urges the barrel 9 and hence the plunger 8 backwards until the ram 4 prevents further backward movement thereof. The backward movement is sufficient to cause the needle 10 to retract into the nozzle 11 so that it is no longer visible to the user and safe from the risk of causing a needle-stick injury. The used injection device can then be safely disposed of.

Blow-back is prevented by the provision of serrations 14 which guide the relative movement of the chamber housing 6 and the outermost housing. These serrations only permit relative movement in one direction, i.e. the chamber housing 6 moving forward with respect to the outermost housing.

Figure 9:
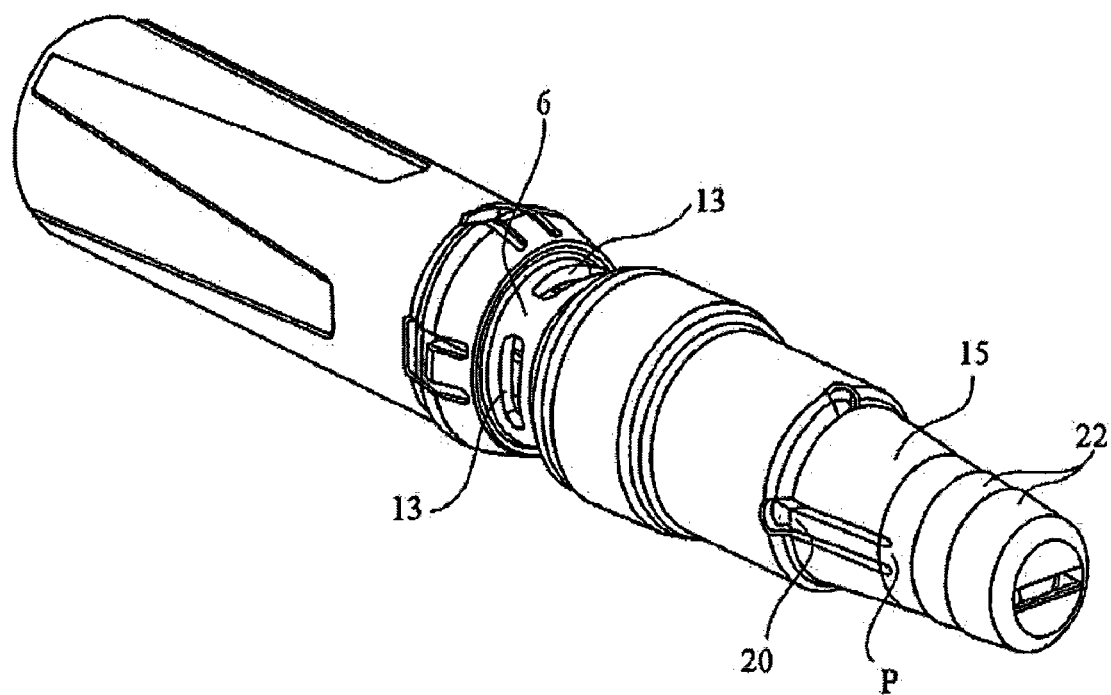
FIG. 9 is a perspective view of the device, including the needle cover.
Figure 10:
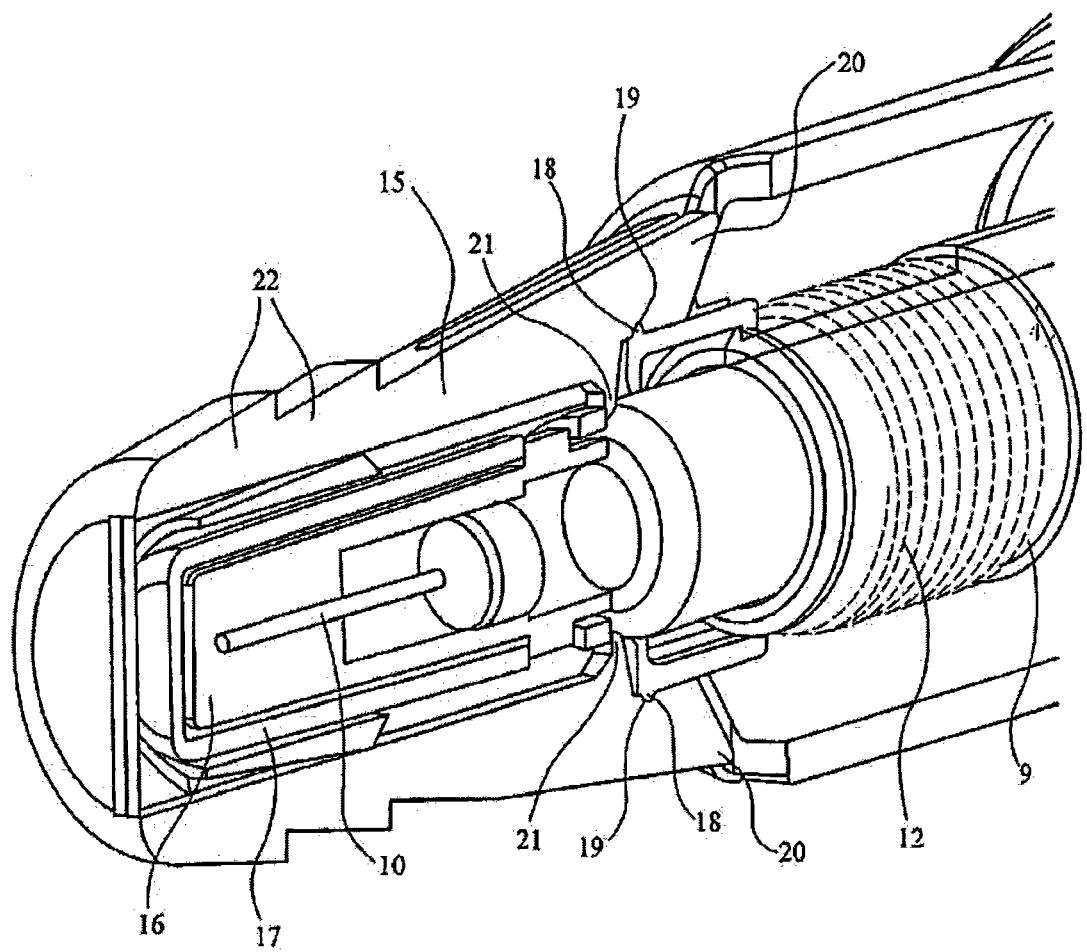
FIG. 10 is perspective view, partly in section, showing detail of the needle cover.

FIG. 9 is a perspective view of the injection device which, in this Figure, includes a needle cover 15. The needle cover is shown in further detail in FIGS. 10 and 11 and is used to protect the needle end of the injection device during transit, storage and before use to deliver an injection.

Regulations require that the needle (which is in direct communication with the medicament in the barrel) is sealed from the outside environment before use. This is achieved by providing protection in the form of a rubber moulding 16 which covers the end of the needle, the rubber moulding 16 being surrounded by a nylon sheath 17. The rubber moulding and nylon sheath (the "needle protection") are fixed with respect to one another by a friction fit between one or more protrusions 16A on the rubber moulding and a corresponding one or more recesses 17A in the nylon sheath.

The nylon sheath and rubber moulding are so firmly fixed on the needle 10 that it is difficult, if not impossible, for a patient to pull them from the needle using his/her fingers alone. Therefore an outer needle cover 15 is provided which not only improves the aesthetic appearance of the injection device, before use, but also serves the function of facilitating the removal of the nylon sheath and rubber moulding.

The needle cover 15 is releasably retained on the front end of the injection device by the fit of annular protrusions 18 on part of the device housing with grooves 19 on the interior of the needle cover. The protrusions 18 and corresponding grooves 19 preferably extend around two equally opposed 60° portions of the circumference of the nozzle 11.

The grooves 19 are located on one or more (preferably equally spaced) flexible legs 20 which are flexible compared to the rest of the needle cover 15, about point P shown in FIG. 9. Forward of each groove 19 is provided an inwardly projecting tab 21 on each flexible leg 20. Each tab 21 abuts the rear of the nylon sheath 17.

Figure 11:
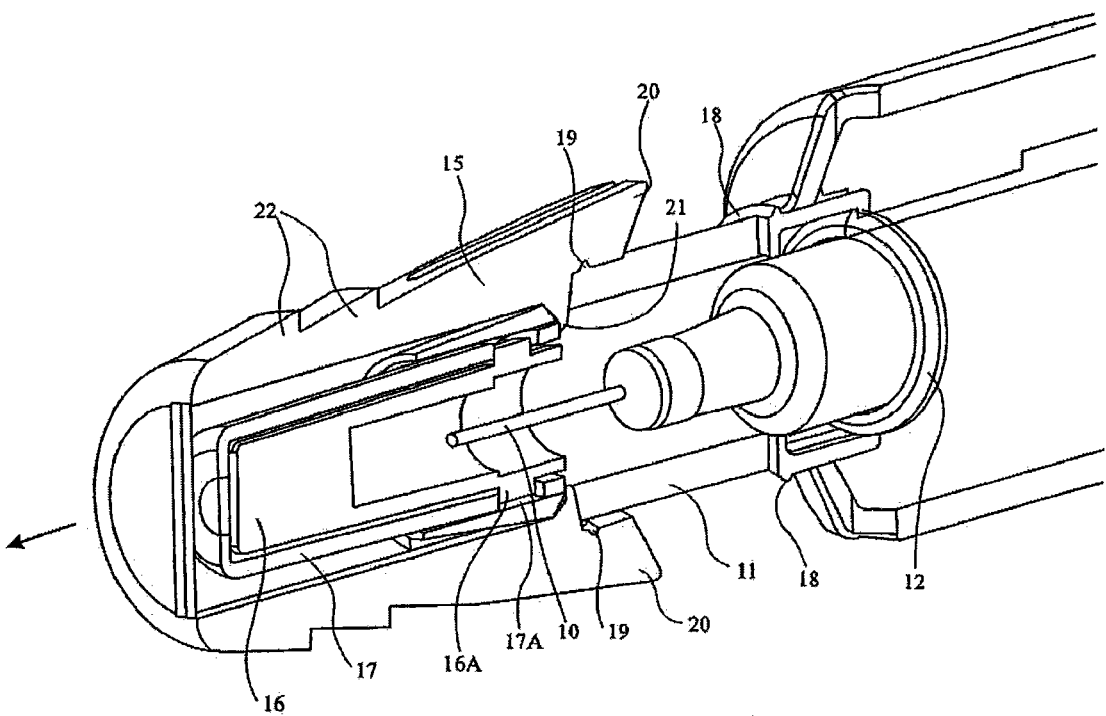
FIG. 11 is perspective view, partly in section, showing detail of the needle cover part way through being removed from the injection device.

Turning now to FIG. 11, when it is desired to remove the needle cover 15 from the device, the user grips the needle cover, preferably in a region having texture or other grip-improving means 22, and pulls in the direction indicated by the arrow in FIG. 11. The flexibility if the legs 20 permits the needle cover to ride over the protrusions 18, disengaging them from the grooves 19. The flexibility of the legs 20 is minimal enough not to cause the tabs 21 to become disengaged from the rear of the nylon sheath 17.

Therefore, as the needle cover 15 is pulled in the direction indicated by the arrow, the tabs 21 are urged against the rear of the nylon sheath 17 and sufficient force can be applied thereby to disengage the needle 10 from the rubber moulding 16. In this way, the entire moulding 16, nylon sheath 17 and needle cover 15 can be removed from the injection device and discarded, so that the injection device is then ready to use.

The invention claimed is:

1. An injection device, comprising:
   an outer housing inside which is located:
      a barrel for holding a dose of a medicament;
      a needle at one end the barrel, the needle and barrel being such that at least part of the needle is axially moveable in and out of said outer housing but is biased to be normally wholly inside said housing;
      a plunger, axially moveable within the barrel;
      an inner housing; and
      an energy source in communication with said inner housing,
      wherein the inner housing is moveable by the energy source and operates in three modes, namely
         a first mode in which the inner housing is in contact with and acts on the barrel other than via said medicament such that, in use, the plunger and barrel move axially so as to move at least part of said needle out of the outer housing, wherein in the first mode the inner housing moves with the plunger and the barrel, wherein in the first mode the inner housing, the plunger and the barrel move relative to the outer housing, and wherein in the first mode the inner housing is intermediate the outer housing and at least a portion of the plunger;
         a second mode in which the inner housing is in direct contact with and acts on the plunger to move the plunger axially but not the barrel such that, in use, said plunger moves axially into said barrel so as to expel medicament through the needle, wherein in the second mode the inner housing moves with the plunger, and wherein the inner housing is intermediate the outer housing and at least portions of both the barrel and the plunger; and
         a third mode in which the inner housing acts on neither the plunger nor the barrel such that, in use, the plunger and barrel retract relative to the inner housing and the outer housing in order to retract the needle into the outer housing, and wherein as a result of said plunger and barrel retracting said needle is retracted such that said at least part of said needle moved out of the outer housing in said first mode is retracted into the outer housing.

2. An injection device as claimed in claim 1 wherein said inner housing includes one or more flexible tags, biased radially inwardly by communication with said outer housing.

3. An injection device as claimed in claim 2 wherein one or more of said tags are situated at the rear end of the inner housing and are biased radially inwardly into communication with the plunger.

4. An injection device as claimed in claim 3 wherein each rear tag is moveable out of communication with the plunger when aligned with a corresponding recess in the outer housing.

5. An injection device as claimed in claim 4 wherein each rear tag is substantially T-shaped.

6. An injection device as claimed in claim 2 wherein one or more of said tags are situated at the forward end of the inner housing and are biased radially inwardly into communication with the barrel.

7. An injection device as claimed in claim 6 wherein each forward tag is moveable out of communication with the barrel when aligned with a corresponding recess in the outer housing.

8. An injection device as claimed in claim 7 wherein each forward tag is substantially L-shaped.

9. An injection device as claimed in claim 1 wherein said energy source is a compressed gas.

10. An injection device as claimed in claim 1 further including means for allowing the inner housing to move axially only forward with respect to the outer housing.

11. An injection device as claimed in claim 10 wherein said means is an arrangement of serrations intermediate the housings.

12. An injection device as claimed in claim 1 wherein said needle is biased to be normally wholly inside said housing by means of a spring intermediate the barrel and the outer housing.

13. An injection device as claimed in claim 1 wherein said needle, barrel and plunger are removable from said device.

14. An injection device as claimed in claim 1 further including a removable needle cover which protects the needle during storage before use.

15. An injection device as claimed in claim 14 wherein said needle cover includes means for pulling a protective rubber sheath or the like from said needle when said needle cover is removed from the device.

16. A method of delivering an injection, comprising:
   providing an injection device comprising:
      a barrel for holding a dose of a medicament;
      a needle at one end the barrel, the needle and barrel being such that at least part of the needle is axially moveable in and out of an outer housing but is biased to be normally wholly inside the outer housing;
      a plunger, axially moveable within the barrel;
      an inner housing; and
      an energy source which acts on the inner housing;
   activating the energy source;
   engaging the barrel with a first portion of the inner housing such that the first portion of the inner housing and a portion of the barrel are in contact with one another other than via said medicament, and moving the barrel and the plunger axially in a first direction by means of the inner housing, wherein the inner housing moves with the plunger and the barrel, and wherein the inner housing, the plunger and the barrel move relative to the outer housing, wherein at least a part of the needle is moved out of the outer housing, and wherein the first portion of the inner housing and a second portion of the inner housing are separated by a first distance while the barrel and the plunger are moved axially in the first direction;
   after moving the barrel and the plunger axially in the first direction, preventing further axial movement of the barrel in the first direction while engaging the plunger with the second portion of the inner housing and moving the plunger axially in the first direction by means of the inner housing, wherein the plunger moves within the barrel causing medicament to be expelled through the needle, wherein the first portion of the inner housing and the second portion of the inner housing are separated by the first distance while the plunger is moved axially in the first direction within the barrel causing medicament to be expelled through the needle, wherein the inner housing is intermediate the outer housing and at least portions of the barrel and the plunger while the plunger is moved axially in the first direction within the barrel, and wherein the inner housing moves with the plunger;
   after causing medicament to be expelled through the needle, disengaging the inner housing from the plunger and retracting the needle into its biased position wholly inside the outer housing, wherein retracting the needle into its biased position wholly inside the outer housing includes retracting the plunger and the barrel relative to the inner housing and the outer housing.

* * * * *